US010080513B2

(12) United States Patent
Stone et al.

(10) Patent No.: US 10,080,513 B2
(45) Date of Patent: Sep. 25, 2018

(54) ACTIVITY ANALYSIS, FALL DETECTION AND RISK ASSESSMENT SYSTEMS AND METHODS

(71) Applicant: The Curators of the University of Missouri, Columbia, MO (US)

(72) Inventors: Erik Edward Stone, Fulton, MO (US); Marjorie Skubic, Columbia, MO (US); Marilyn Rantz, Rocheport, MO (US); Mihail Popescu, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 15/424,375

(22) Filed: Feb. 3, 2017

(65) Prior Publication Data

US 2017/0143240 A1    May 25, 2017

Related U.S. Application Data

(63) Continuation of application No. 14/169,508, filed on Jan. 31, 2014, now Pat. No. 9,597,016, which is a
(Continued)

(51) Int. Cl.
*A61B 5/103* (2006.01)
*A61B 5/11* (2006.01)
(Continued)

(52) U.S. Cl.
CPC .......... *A61B 5/1128* (2013.01); *A61B 5/0013* (2013.01); *A61B 5/0022* (2013.01); *A61B 5/112* (2013.01); *A61B 5/1113* (2013.01); *A61B 5/1117* (2013.01); *A61B 5/746* (2013.01); *G06K 9/00342* (2013.01); *G06T 7/194* (2017.01); *G06T 7/215* (2017.01); *G06T 7/285* (2017.01);
(Continued)

(58) Field of Classification Search
CPC ...... A61B 5/4528; A61B 5/1071; A61B 5/103
USPC ........................................................ 600/595
See application file for complete search history.

(56) References Cited

U.S. PATENT DOCUMENTS 5,231,483 A * 7/1993 Sieber .................... G01S 3/807
                                                          348/169
5,309,921 A   5/1994 Kisner et al.
(Continued)

FOREIGN PATENT DOCUMENTS

WO    2013058985 A1    4/2013
WO    2013066601 A1    5/2013

*Primary Examiner* — Daniel Cerioni
(74) *Attorney, Agent, or Firm* — Sandberg Phoenix & von Gontard P.C.

(57) ABSTRACT

A method for determining the risk of a person falling is provided. The method includes acquiring depth image data that comprises a plurality of frames that depict a person walking through a home, and extracting a foreground object from the depth image data. The method additionally includes generating a three-dimensional data object based on the foreground object, and identifying a walking sequence from the three-dimensional data object. The method further includes generating one or more gait parameters from the identified walking sequence, and comparing the one or more gait parameters against a standard clinical measure of the one or more gait parameters to determine a level of risk at which the person is of falling.

5 Claims, 6 Drawing Sheets

Related U.S. Application Data continuation-in-part of application No. 13/871,816, filed on Apr. 26, 2013, now Pat. No. 9,408,561.

(60) Provisional application No. 61/788,748, filed on Mar. 15, 2013, provisional application No. 61/649,770, filed on May 21, 2012, provisional application No. 61/687,608, filed on Apr. 27, 2012.

(51) Int. Cl.
  *A61B 5/00* (2006.01)
  *G06T 7/194* (2017.01)
  *G06T 7/285* (2017.01)
  *G06K 9/00* (2006.01)
  *G06T 7/215* (2017.01)

(52) U.S. Cl.
  CPC ............... *G06T 2207/10028* (2013.01); *G06T 2207/30196* (2013.01); *G06T 2207/30241* (2013.01)

(56) References Cited

U.S. PATENT DOCUMENTS

| | | |
|---|---|---|
| 6,002,994 A | 12/1999 | Lane et al. |
| 6,915,008 B2 | 7/2005 | Barman et al. |
| 7,420,472 B2 | 9/2008 | Tran |
| 7,502,498 B2 | 3/2009 | Wen et al. |
| 7,843,351 B2 | 11/2010 | Bourne et al. |
| 2003/0058111 A1 | 3/2003 | Lee et al. |
| 2003/0059081 A1 | 3/2003 | Trajkovic |
| 2003/0085992 A1 | 5/2003 | Arpa et al. |
| 2004/0030531 A1 | 2/2004 | Miller et al. |
| 2004/0119716 A1 | 6/2004 | Park et al. |
| 2004/0228503 A1 | 11/2004 | Cutler |
| 2005/0088515 A1 | 4/2005 | Geng |
| 2005/0094879 A1 | 5/2005 | Harville |
| 2006/0055543 A1 | 3/2006 | Ganesh et al. |
| 2007/0003146 A1 | 1/2007 | Ko et al. |
| 2007/0085690 A1 | 4/2007 | Tran |
| 2007/0152837 A1 | 7/2007 | Bischoff et al. |
| 2007/0263900 A1 | 11/2007 | Medasani et al. |
| 2008/0117060 A1 | 5/2008 | Cuddihy et al. |
| 2009/0079559 A1 | 3/2009 | Dishongh et al. |
| 2009/0079813 A1 | 3/2009 | Hildreth |
| 2009/0089089 A1 | 4/2009 | Jang et al. |
| 2010/0302043 A1 | 12/2010 | Skubic et al. |
| 2012/0019643 A1 | 1/2012 | Gideon et al. |
| 2012/0101411 A1 | 4/2012 | Hausdorff et al. |
| 2012/0172681 A1 | 7/2012 | Sun et al. |
| 2012/0253201 A1 | 10/2012 | Reinhold |
| 2014/0303460 A1 | 10/2014 | Corley et al. |

* cited by examiner

ACTIVITY ANALYSIS, FALL DETECTION AND RISK ASSESSMENT SYSTEMS AND METHODS

CROSS-REFERENCE TO RELATED APPLICATIONS

This application is a continuation of U.S. patent application Ser. No. 14/169,508 filed on Jan. 31, 2014, which is claims priority to U.S. patent application Ser. No. 13/871,816 filed on Apr. 26, 2013, which claims priority under 35 U.S.C. § 119(e) to provisional applications, including Application No. 61/788,748 entitled "Activity Analysis, Fall Detection And Risk Assessment Systems And Methods" filed on Mar. 15, 2013; Application No. 61/649,770 entitled "Activity Analysis, Fall Detection And Risk Assessment Systems And Methods" filed on May 21, 2012; and Application No. 61/687,608 entitled "Activity Analysis, Fall Detection, and Risk Assessment Using Depth Camera for Eldercare and Other Monitoring Applications" filed on Apr. 27, 2012. The disclosure of the above applications are incorporated herein by reference in their entirety.

FIELD

The present invention relates to methods and systems for activity monitoring of a patient, and more specifically, to methods and systems for obtaining measurements of temporal and spatial gait parameters of the patient for use in health risk assessment.

BACKGROUND

The statements in this section merely provide background information related to the present disclosure and cannot constitute prior art.

Human activity analysis from video is an open problem that has been studied within the areas of video surveillance, homeland security, and eldercare. For example, the monitoring of human activity is often employed in the medical industry to detect any abnormal or dangerous events, such as falls and/or the risk of falls for a patient. Various parameters, such as gait parameters and/or other locomotive measurements corresponding to a medical patient, are often monitored and considered indispensable in the diagnosis of frailty and fall risk, and in particular, when providing medical care for the elderly.

Falls are a significant issue among the elderly. For example, it is estimated that between 25-35% of people 65 years and older fall each year, and many of such falls result in serious injuries, such as hip fractures, head traumas, and the like. Moreover, the medical costs associated with such falls are astronomical. In the year 2000, it is estimated that over $19 billion dollars were spent treating fall-related injuries for the elderly. Such costs do not account for the decreased quality of life and other long term effects often experienced by many elderly patients after suffering a fall.

Thus, a low-cost monitoring system that would allow for continuous, standardized assessment of fall risk can help address falls and the risk of falls among older adults. Moreover, to enable older adults to continue living longer, in particular, in an independent setting, and thus reduce the need for expensive care facilities, low-cost systems are needed that detect both adverse events such as falls, and the risk of such events.

It is with these concepts in mind, among others, that various embodiments of the present disclosure were conceived.

SUMMARY

The present disclosure provides a method for determining the risk of a person falling is provided. In various embodiments, the method includes acquiring depth image data that comprises a plurality of frames that depict a person walking through a home, and extracting a foreground object from the depth image data. In various embodiments, the method additionally includes generating a three-dimensional data object based on the foreground object, and identifying a walking sequence from the three-dimensional data object. In various embodiments, the method further includes generating one or more gait parameters from the identified walking sequence, and comparing the one or more gait parameters against a standard clinical measure of the one or more gait parameters to determine a level of risk at which the person is of falling.

Further areas of applicability of the present teachings will become apparent from the description provided herein. It should be understood that the description and specific examples are intended for purposes of illustration only and are not intended to limit the scope of the present teachings.

DRAWINGS

The foregoing and other objects, features, and advantages of the present disclosure set forth herein will be apparent from the following description of exemplary embodiments of those inventive concepts, as illustrated in the accompanying drawings. It should be noted that the drawings are not necessarily to scale; however, the emphasis instead is being placed on illustrating the principles of the inventive concepts. Also in the drawings, the like reference characters refer to the same parts throughout the different views. The drawings depict only exemplary embodiments of the present disclosure and, therefore, are not to be considered limiting in scope.

DETAILED DESCRIPTION

Figure 1:
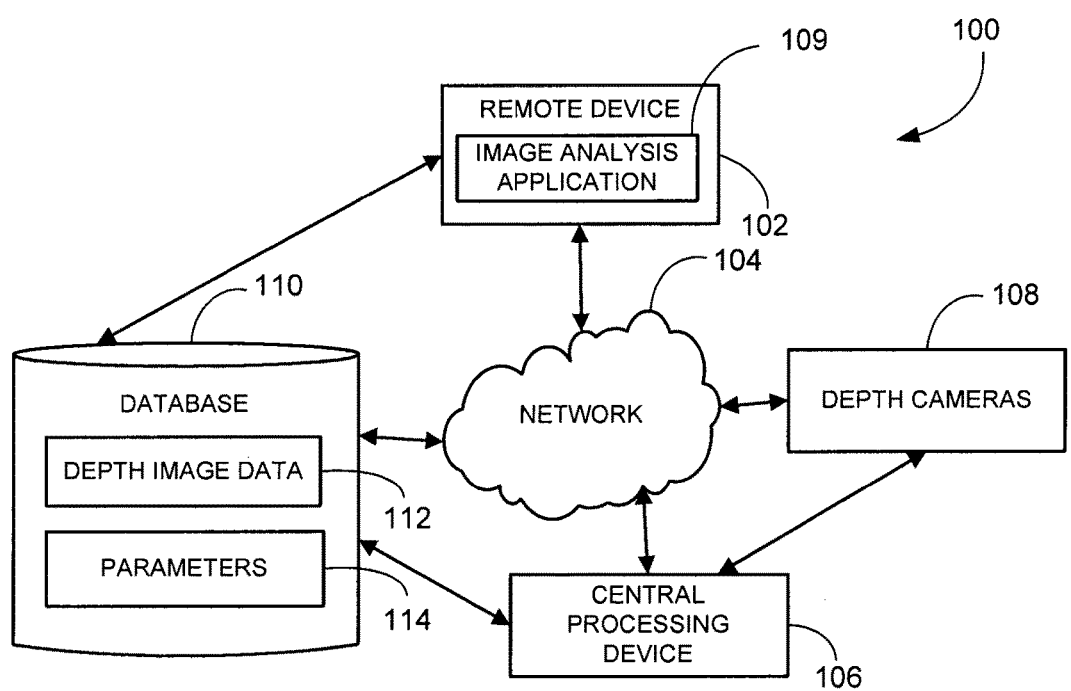
FIG. 1 is a block diagram illustrating a computing environment for obtaining one or more parameters to perform health risk assessments, according to various embodiments of the present disclosure.

The following description is merely exemplary in nature and is in no way intended to limit the present teachings, application, or uses. Throughout this specification, like reference numerals will be used to refer to like elements.

Various embodiments of the present disclosure include methods and corresponding systems for performing health risk assessments for a patient in the home environment. In various embodiments, depth image data for a medical patient is obtained and subsequently used to generate one or more parameters, such as temporal and spatial gait parameters. Subsequently, the generated parameters can be used with other medical information related to the patient, such as electronic health records, to perform various health risk assessments, such as for example, alerting health care professionals of alarming trends or other health risks associated with the patient.

Falls represent a substantial health risk among the elderly, as the risk of falls generally increases with age. It is estimated that one out of every three older adults (age 65 and over) falls each year, many of which suffer serious injuries, such as hip fractures, head traumas, etc. Typically, the result of such falls is a reduction in a person's gait ability, such as a reduction in mobility and independence, all of which can ultimately increase the risk of early death. The causes of such falls are known as "risk" factors. Although, generally, no single risk factor can be considered the single cause of a given fall, the greater the number of risk factors to which an individual is exposed, the greater the probability of a fall and the more likely the results of the fall will threaten the person's independence.

Research has shown that gait parameters, which describe the pattern of movement in animals and humans, are indispensable in assessing risk factors, making fall risk assessments, the diagnosis of fall risk, or the like. For example, studies have indicated that gait parameters can be predictive of future falls and adverse events in older adults and, further, that scores on certain mobility tests are good indicators of fall risk. Despite these findings, gait parameters and mobility tests are generally assessed infrequently, if at all, and are typically monitored through observation by a clinician with a stop watch or a clinician using equipment in a physical performance lab, both of which are expensive and labor-intensive. Such sparse, infrequent evaluations can not be representative of a person's true functional ability. Various embodiments of the present disclosure involve methods and systems for monitoring patient gait parameters continuously, during everyday activity, in a cost-effective, efficient manner. Monitoring such parameters and/or activities can offer significant benefits for fall risk and mobility assessment.

FIG. 1 illustrates an example system 100 for obtaining depth image data and subsequently processing the depth image data to generate gait parameters (both temporal and spatial) for use in health risk assessment, in accordance with various embodiments of the present disclosure. The system 100 is an example platform in which one or more embodiments of the methods can be used. However, it is contemplated that such methods and/or processes can also be performed on other conventional computing platforms, as are generally known in the art.

Referring now to FIG. 1, a user, such as an administrator, clinician, researcher, family member, etc., can use a remote device 102 to receive and/or otherwise obtain depth image data from one or more depth camera(s) 108. Depth image data can include any type of data captured from a camera capable of being processed to generate a representation of an object, and in particular, a patient in a given location, such as a three-dimensional point cloud representation, of that person or patient. In one embodiment, the depth image data can include audio and can be captured in an audio format, such as by one or more microphones associated with the depth cameras 108, or other type of recording device. The remote device 102 can be located in a living unit, outside a living unit but in a living community, or in a location outside the living community such as a hospital setting, and can include various hardware and accompanying software computing components that can be configured to receive and/or otherwise capture and process the depth image data. For example, as illustrated, the remote device 102 can execute an image analysis application 109 that receives depth image data associated with a particular patient. Subsequently, the image analysis application 109 can process the depth image data to extract, generate and/or otherwise compute temporal and/or spatial gait parameters of a patient for use in various health risk assessments. The image analysis application 109 can provide the temporal and/or spatial gait parameters and corresponding risk assessments for display, such as for example, as part of a graphical user interface.

A user can use the remote device 102 as a stand-alone device to compute temporal and spatial gait parameters for use in health risk assessment, or can use the remote device 102 in combination with a central computing device 106 available over a network 104. In some embodiments, the central computing device 106 can also be under the control of the same user but at a remote location, such as a location outside of the living community. For example, according to various embodiments, the remote device 102 can be in a client-server relationship with the central computing device 106, a peer-to-peer relationship with the central computing device 106, or in a different type of relationship with the central computing device 106. In one embodiment, the client-server relationship can include a thin client on the remote device 102. In another embodiment, the client-server relationship can include a thick client on the remote device 102.

The remote device 102 can communicate with the central processing device 106 over a network 104, which can be the Internet, an intranet, a local area network, a wireless local network, a wide area network, or another communication network, as well as combinations of networks. For example, the network 104 can be a Mobile Communications (GSM) network, a code division multiple access (CDMA) network, an Internet Protocol (IP) network, a Wireless Application Protocol (WAP) network, a WiFi network, or an IEEE 802.11 standards network, as well as various combinations thereof. Other conventional and/or later-developed wired and wireless networks can also be used.

The central computing device 106 can include various hardware and accompanying software computing components to operate in substantially the same manner as the remote device 102 to receive depth image data. In one embodiment, the central computing device 106 can be a single device. Alternatively, in another embodiment, the central computing device 106 can include multiple computer systems. For example, the multiple computer systems can be in a cloud computing configuration.

One or more depth cameras 108 and/or sets of depth cameras 108 can be included in the system 100 to generate video signals of the objects (e.g., persons) residing in the living unit. The depth cameras 108 and/or sets of depth cameras 108 can include various computing and camera/lense components such as an RGB camera, infrared sensitive camera, from which a depth image and/or depth image data can be obtained. Other computing and/or camera components can also be included, as are generally known in the art. An example configuration of one or more depth cameras 108 in various living areas is described in greater detail below.

The remote device 102, the central computing device 106, or both can communicate with a database 110. The database 110 can include depth image data 112 and parameters 114. The depth image data 112 can be stored based on the video signals generated by the depth cameras 108. In general, the depth image data 112 can include depth data, such as a pattern of projected light, from which a depth image can be produced. In some embodiments, the video signals generated by the depth cameras 108 prior to converting the images to depth images are not stored in the database 110 or elsewhere in the system 100. The processing performed on the depth image data 112 can be stored as the parameters 114 in the database 110. The depth image data 112 can be used to track the person's activity as described in greater detail below.

While various embodiments of the present disclosure have been described as being performed using multiple devices within a computing environment, such as computing environment 100 shown in FIG. 1, it is contemplated that such various embodiments can be performed locally, using only a single device, such as the central processing device 106, and in such cases the remote device 102 is integrated into or otherwise in direct connection with the central processing device 106. In such an arrangement, the central processing device 106 can be in direct communication with the depth cameras 108 and the database 110.

Figure 2:
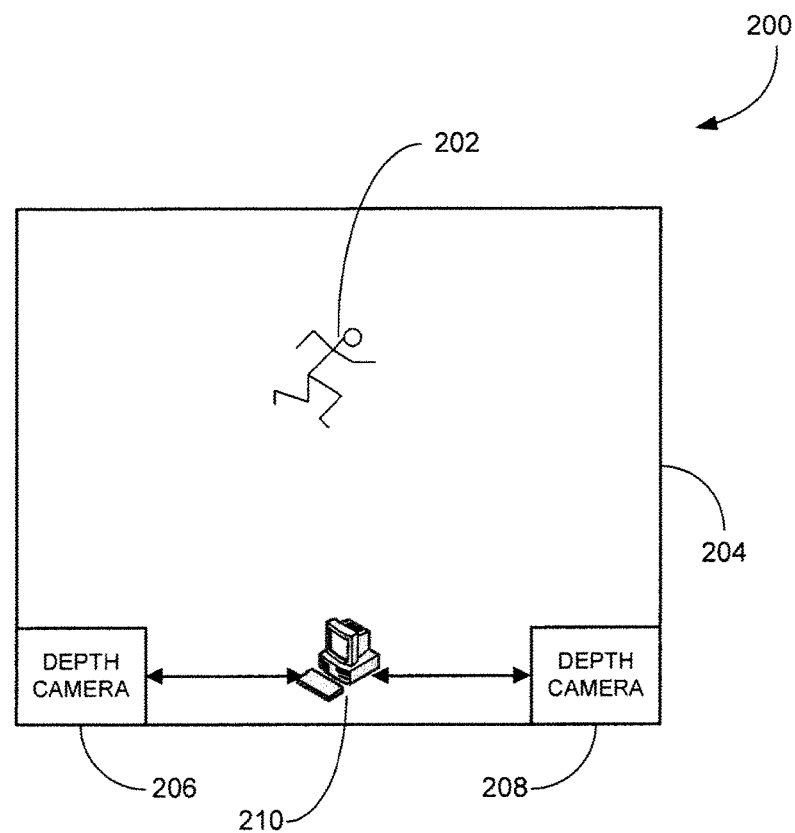
FIG. 2 is a block diagram illustrating an example living unit, according to various embodiments of the present disclosure.

FIG. 2 illustrates an example living unit 200, according to an example embodiment. The living unit 200 is shown to have a person 202 (e.g., a medical patient being monitored) in an area 204 of the living unit 200. The depth cameras 108 of FIG. 1 are shown as two depth cameras 206, 208, although the system can be implemented using a single depth camera 208 or more than two depth cameras. These depth cameras 206, 208 can be deployed in the living unit 200 to generate video signals depicting the person 202 from different views in the area 204.

According to one embodiment, the depth cameras 206, 208 can be Microsoft Kinect™ cameras that are placed at various locations within the area 204, capable of performing 3D motion tracking using a skeletal model, gesture recognition, facial recognition, and/or voice recognition. Each Microsoft Kinect™ camera can include one or more sensors, an IR sensitive camera, or the like, that use a pattern of actively emitted infrared light in combination with a complementary metal-oxide-semiconductor ("CMOS") image sensor and/or an IR-pass filter to obtain depth image data, such as a depth image, that is generally invariant to ambient lighting. Each Microsoft Kinect™ camera can also include a standard RGB camera and/or other camera components as are generally known in the art.

For example, in one particular embodiment, the depth cameras 206, 208 can capture image depth data of the person 202, such as 3D motion tracking data at 30 frames per second, all of which can be invariant to changes in visible light. In some embodiments, the depth cameras 206, 208 are static in the area 204. As such, the depth cameras 206, 208 cannot physically move locations within the living unit 200, change focus, or otherwise alter their view of the area 204. Alternatively, in other embodiments, the depth cameras 206, 208 can be deployed to generate additional video signals of the person 202. The depth cameras 206, 208 can then be appropriately deployed in the area 204 or elsewhere in the living unit 200 to generate video signals of the person 202. The video signals generated by the depth cameras 206, 208 can be provided to the remote device 102 shown in the form of a computing system 210. As shown, the computing system 210 is deployed in the living unit 200. However, the computing system 210 can be elsewhere. Any depth image data 112 captured from the depth cameras 206, 208 (e.g., a Microsoft Kinect™ camera) can be used to extract or otherwise generate gait parameters of walking speed, right/left stride time and/or right/left stride length, stride to stride variability, trunk sway, gait asymmetry, entropy, and the like. Entropy is used as a measure of regularity in gait. A comprehensive explanation of Entropy is described in an Appendix entitled: "In-Home Measurement Of The Effect Of Strategically Weighted Vests On Ambulation," which is incorporated by reference in its entirety herein.

Figure 3:
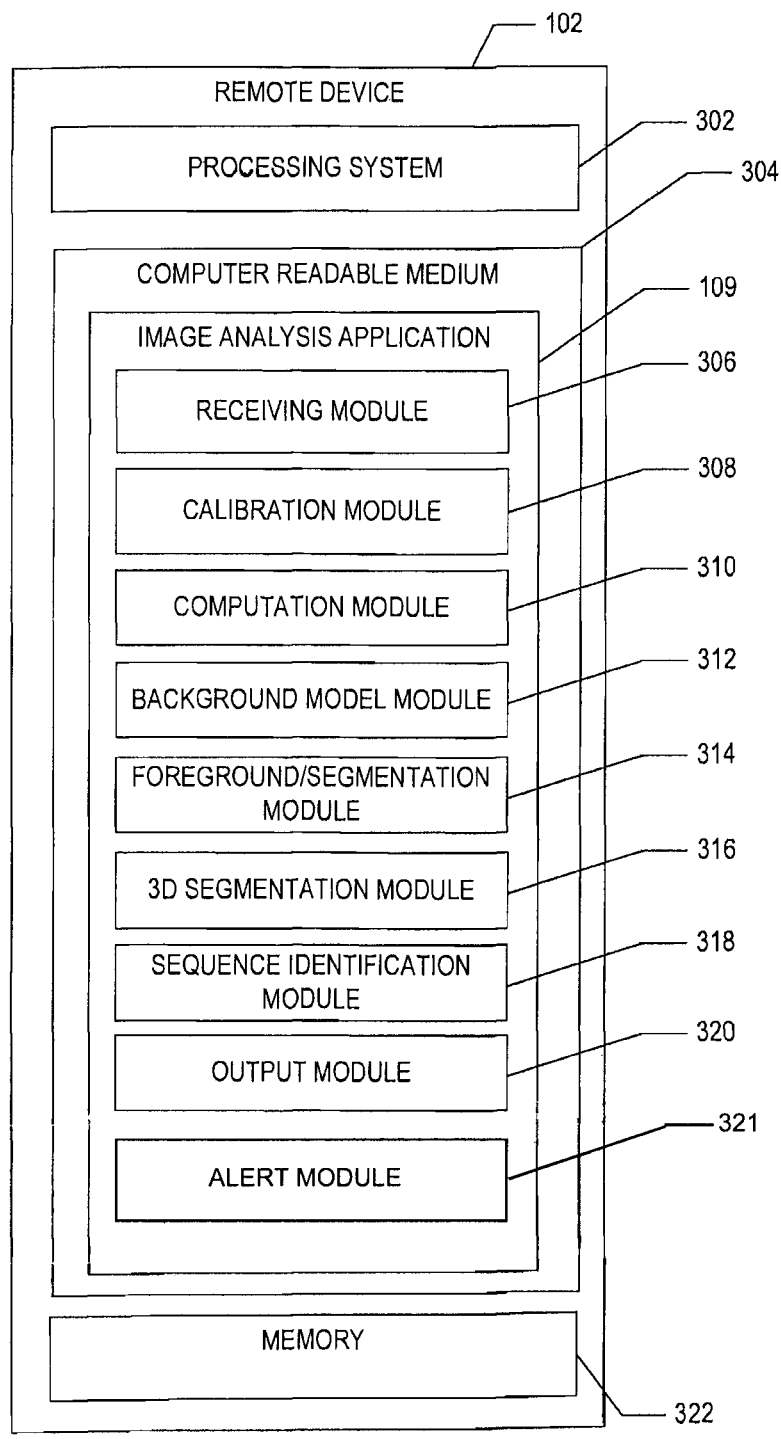
FIG. 3 is a block diagram illustrating a remote device, according to various embodiments of the present disclosure.

FIG. 3 is an example block diagram illustrating the various hardware and/or software components of the remote device 102 according to one exemplary embodiment of the present disclosure. The remote device 102 can include a processing system 302 that can be used to execute the image analysis application 109 that receives depth image data (i.e. depth image data 112) and generates one or more temporal and/or spatial gait parameters for health risk assessment. The processing system 302 can include memory and/or be in communication with a memory 322, which can include volatile and/or non-volatile memory. The processing system 302 can also include various other computing components.

The remote device 102 can include a computer readable media ("CRM") 304, which can include computer storage media, communication media, and/or another available computer readable media medium that can be accessed by the processing system 302. For example, CRM 304 can include non-transient computer storage media and communication media. By way of example and not limitation, computer storage media includes memory, volatile media, non-volatile media, removable media, and/or non-removable media implemented in a method or technology for storage of information, such as machine/computer readable/executable instructions, data structures, program modules, or other data. Communication media includes machine/computer readable/executable instructions, data structures, program modules, or other data. The CRM 304 is configured with the image analysis application 109. The image analysis application 109 includes program instructions and/or modules that are executable by the processing system 302. Generally, program modules include routines, programs, instructions, objects, components, data structures, etc., that perform particular tasks or implement particular abstract data types.

According to various embodiments, the image analysis application 109 can include a receiving module 306 that receives depth image data 112 from one or more depth cameras 108. For example, the receiving module 306 can receive a pattern of projected infrared light from a Microsoft Kinect™ camera. More particularly, the depth image data 112 received from the Microsoft Kinect™ camera (at 30 frames per second) can be an 11-bit 640×480 image which is invariant to visible lighting. The precision of the distance measurement for each pixel is dependent on the distance from the Kinect™, with the precision decreasing from approximately one centimeter at two meters to approximately ten centimeters at six meters. The depth image data 112 can be stored in a database or other type of data store, where each data entry in the database corresponds to a walk and/or walk sequence identified in a particular space, such as an apartment corresponding to the patient.

Optionally, before the receiving module 306 receives any depth image data 112 from the depth cameras 108, a calibration module 308 can estimate calibration parameters for the depth cameras 108. For example, in the embodiment in which the depth cameras 108 are Microsoft Kinect™ cameras, intrinsic, distortion, and stereo parameters for the IR and the RGB cameras of the Kinect™ can be estimated according to a calibration pattern, such as a checkerboard calibration pattern and/or the like. Subsequently, calibration of any depth image data 112 returned from the Microsoft Kinect™ can be performed, as the depth image data 112 returned from the Kinect™ can require some form of transformation to obtain usable and accurate distances. For example, the following equations can be used to transform a raw Kinect™ depth image data depth value, D, an integer value typically in the range [660, 1065], for a given pixel, (x, y), to a distance, d:

$$d = \frac{b}{f - D'} \quad (1)$$

$$D' = D(1 + k_1 r + k_2 r^2) + k_3 x' + k_4 y' \quad (2)$$

$$r = \sqrt{(x')^2 + (y')^2} \quad (3)$$

where x' and y' are the normalized pixel coordinates computed using the intrinsic and distortion parameters of the IR camera. The parameters b, f, $k_1$, $k_2$, $k_3$, and $k_4$ are optimized over a large (~3,000) set of training points and the equation attempts to adjust for distortion effects. The training points are obtained by placing a large checkerboard calibration pattern in the environment, while moving the Kinect™ over a large range of distances and viewing angles with respect to the pattern. Using the known intrinsic parameters of the IR camera of the Kinect™ the position of the calibration pattern with respect to the camera in each frame can be estimated. Simultaneously, the values associated with the pattern in the depth image data can be recorded. Following collection of the training data, a global optimization is performed using, for example, the CMA-ES algorithm although other optimization algorithms can be used. The CMA-ES algorithm is an optimization algorithm used to find a solution that minimizes an objective function. Example values for the parameters {b, f, $k_1$, $k_2$, $k_3$, $k_4$} used to transform the raw depth values to inches are {14145.6, 1100.1, 0.027, −0.014, 1.161, 3.719}.

After receiving, and optionally calibrating, depth image data, the receiving module 306 can automatically initiate a computation module 310 that analyzes, parses, and/or otherwise processes the depth image data to generate one or more parameters by executing one or more algorithms and/or equations. For example, the computation module 310 can extract gait parameters, such as walking speed, stride time, and stride length from the depth image data (e.g., a 3-dimensional representation of objects within a space, such as a room within a home or apartment).

A brief description of the various computations that can be performed by the computation module 310 will now be provided. Initially, foreground objects, represented as a set of 3D points, can be identified from depth image data using a dynamic background subtraction technique. Subsequently, a tracking algorithm can be used to track any extracted 3D objects and/or points. Walks can then be identified from the path histories of the tracked objects. More particularly, a set of criteria including path straightness, speed, duration, and distance can be used to identify suitable walks from the path histories.

Accordingly, initially, in one embodiment, the computation module 310 can initiate a background model module 312, which executes a background subtraction algorithm, optionally, in conjunction with a background model initialization algorithm and/or a background model updating algorithm, to generate a background model. Specifically, the background module 312 can generate the background model from the depth image data 112 captured by the depth cameras 108. In one embodiment, the background modeling algorithm can use a mixture of distributions approach typically run at 15 frames per second. The distributions are simple ranges defined by a minimum and maximum value. The background model consists of $K_b$ background and $K_f$ foreground distributions for each pixel in the disparity image. Each distribution, $D_k(x,y)$, is defined by three floating point values, an upper bound, a lower bound, and a weight:

$$D_k(x,y) = \{[l_k(x,y), u_k(x,y)], W_k(x,y)\}$$

The background modeling algorithm can be initialized over a set of training frames using the procedure defined in "Algorithm 1—Background Model Initialization" as described below:

Algorithm 1 - Background Model Initialization

CONSTANTS: Wmax , Winit , ΔW
INPUT: set of training disparity images, I
SET: Wj(x,y) = 0, j=1:$K_b$+$K_f$ , x=1:width, y=1:height
for each image i∈ I
for each pixel $p_i$(x,y) , x=1:width, y=1:height
if $p_i$(x,y) = valid disparity value
for each distribution $D_j$(x,y), j=1:$K_b$
if $W_j$(x,y) > 0 and $p_i$(x,y) matches [$l_j$(x,y), $u_j$(x,y)]
//Update the distribution and weight
$W_j$(x,y) = min( $W_j$(x,y) + ΔW, $W_{max}$)
$l_j$(x,y) = min( $p_i$(x,y) −1, $l_j$(x,y) )
$u_j$(x,y) = max( $p_i$(x,y) +1, $u_j$(x,y))
if no distributions were matched
//Replace least weight BACKGROUND distribution
j = arg min $W_k$(x,y)
    k=1:$K_b$
$W_j$(x,y) = $W_{init}$
$l_j$(x,y) = $p_i$(x,y) − 1
$u_j$(x,y) = $p_i$(x,y) + 1 where $W_{max}$ represents the maximum allowed weight a distribution can have; $W_{init}$ represents the initial weight given to a new distribution; ΔW is the increment added to a distribution's weight if the distribution is matched. Further, Dj(x,y) refers to distribution j for pixel x,y and contains and $W_j$(x,y) refers to the weight of distribution j for pixel x,y. The variable $l_j$(x,y) refers to the lower bound of distribution j for pixel x,y and $u_j$(x,y) refers to the lower bound of distribution j for pixel x,y. Finally, $p_i$(x,y) refers to the value of pixel x,y in image i.

It should be noted that only background distributions are initialized over the training frames. The foreground distributions are left uninitialized with $W_k$(x,y)=0. Once initialized, the model is updated at each new frame using the procedure defined in "Algorithm 2—Background Model Updating" as described below:

Algorithm 2 - Background Model Updating

CONSTANTS: $W_{max}$ , $W_{init}$ , ΔW , $W_{adapt}$ , ΔR
INPUT: new disparity image, i
for each pixel $p_i$(x,y) , x=1:width, y=1:height
if $p_i$(x,y) = valid disparity value
for each distribution $D_j$(x,y), j=1:$K_b$+$K_f$
if $W_j$(x,y) > 0 and $p_i$(x,y) matches [$l_j$(x,y), $u_j$(x,y)]
//Update the distribution range and weight
$W_j$(x,y) = min( $W_j$(x,y) + ΔW, $W_{max}$)
$l_j$(x,y) = min( $p_i$(x,y) −1, $l_j$(x,y) +ΔR)
$u_j$(x,y) = max( $p_i$(x,y) +1, $u_j$(x,y) − ΔR)

Algorithm 2 - Background Model Updating

```
        else
            //Decay distribution weight
            W_j(x,y) = max( W_j(x,y) − ΔW, 0)
        if no distributions were matched
            //Replace least weight FOREGROUND distribution
            j =   arg min   W_k (x, y)
                k=K_b:K_b + K_f
            W_j(x,y) = W_init
            l_j(x,y) = p_i(x,y) − 1
            u_j(x,y) = p_i(x,y) + 1
        for each distribution D_j(x,y), j= K_b+1:K_b+K_f
            //Adapt FOREGROUND to BACKGROUND
            if W_j(x,y) > W_adapt
                k = arg min W_p (x, y)
                    p=1:K_b
                W_k(x,y) = W_j(x,y)
                l_k(x,y) = l_j(x,y)
                u_k(x,y) = u_j(x,y)
                W_j(x,y) = 0
```

In Algorithm 2, $W_{max}$ and $W_{min}$ are the same as described for Algorithm 1. $\Delta W$ is a value that, in addition to being added to a distribution's weight if a distribution is matched, can be subtracted from a distribution's weight if the distribution is not matched given the pixel has a valid depth value. $W_{adapt}$ represents the threshold at which a foreground distribution will be converted to a background distribution. $\Delta R$ represents a value that is used to keep the upper and lower bounds of a distribution from simply growing apart over time.

A foreground/segmentation module 314 can process any background models (i.e., the frames) generated by the background model module 312 to extract, segment, classify and/or otherwise identify a foreground and/or foreground pixels. Thus, the foreground/segmentation module 314 can classify a pixel as foreground and/or as background.

More particularly, given the background model, for each pixel, the first step of foreground segmentation is to compare the disparity value of each pixel from the current frame against its background model. If the disparity value of a pixel is found to match one of its active ($W_k(x,y)>0$) background distributions, then the pixel is classified as background; otherwise the pixel is classified as foreground. All pixels for which a valid disparity value is not returned are assumed to be background. A pixel is found to match a distribution if it lies within the range defined by the distribution, or its distance from the range is less than a threshold T (for this work T=0.25). Following such an initial classification, a block-based filtering algorithm can be applied to eliminate noise. Finally, morphological smoothing and hole-filling is used to further clean the image.

A 3D Segmentation module 316 can generate three-dimensional ("3D") models for tracking from any extracted foreground. Specifically, given the extracted foreground for a frame, 3D objects are formed and evaluated for tracking. In one embodiment, the intrinsic and extrinsic calibration parameters generated by the calibration module 308 can be processed by the computation module 310 to convert the 3D foreground pixels into a set of 3D points.

Following conversion of the foreground pixels to a set of 3D points, object segmentation by the 3D segmentation module 316 is performed. More particularly, the set of the 3D points can be projected onto a discretized (1×1 inch) ground plane and single-linkage clustering is used to group the points into objects. The ground plane is discretized to limit the number of points considered by the clustering algorithm, and a distance of six inches is used for the single-linkage clustering threshold. In one embodiment, various parameters can be extracted from each 3D object (a cloud of 3D points), at each frame: avg x/y/z, max x/y/z, min x/y/z, covariance matrix, time stamp, ground plane projection of points below 22 inches and a correlation coefficient based on such a projection.

An estimate of volume can be obtained for each 3D object by summing the range of Z values for each location in the discretized ground plane that are part of the object. Any objects with a volume estimate greater than or equal to a threshold, V, are considered valid and retained for tracking, while any objects with volume estimates less than V are discarded. (For this work, V=725.) The 3D objects obtained from the current frame are compared against a set of currently tracked objects. All those new objects which match an existing object based on location and volume are used to update the existing tracked object, while all those that do not match an existing object are used to create new entries in the tracked object list. Each tracked object maintains a history of up to 30 seconds. Tracked objects are discarded if not updated for 20 seconds.

A sequence identification module 318 can be used to automatically identify walking sequences from the 3D objects (e.g. the tracked objects). Subsequently, the analyzed walking sequences can be processed by the computation module 310 to generate various gait parameters such as, in one embodiment, a walking speed, average speed, peek speed, stride time (e.g. individual stride time), and/or stride length (e.g. individual stride length), average stride length, height of the person walking, among others.

Figure 5:
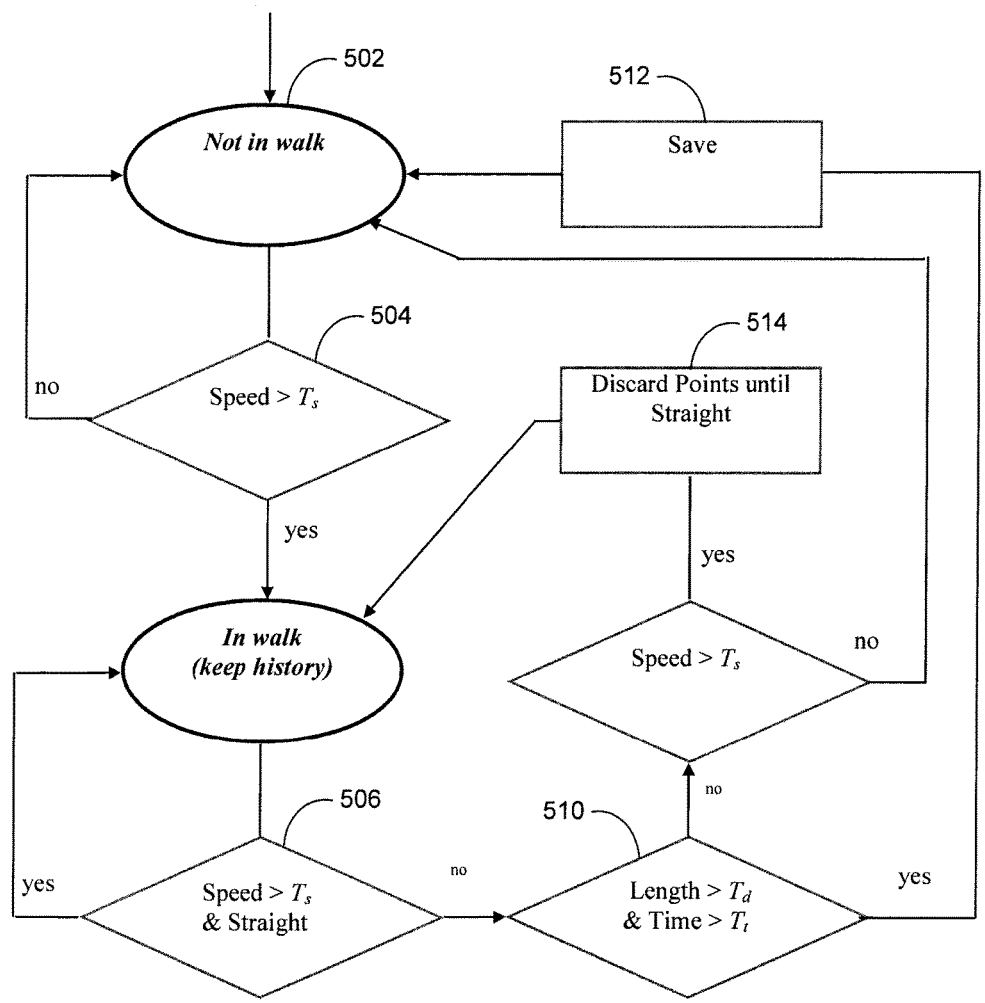
FIG. 5 is a flowchart illustrating walk sequences, according to various embodiments of the present disclosure.

In one embodiment, as illustrated in FIG. 5, the identification of walk sequences can be determined using the histories of the tracked 3D objects. After each new frame, the history of each tracked object is evaluated to determine if a walk has just started, ended, or is currently in progress. For example, upon initialization of a 3D object in the tracked object set, the object is assumed to "not be in a walk" (operation 502). The object stays in the "not in walk" state until the speed of the object goes above a threshold, $T_s$. Thus, the state of the object changes from "not in walk" to "in walk" (operation 504). The object remains in such a state until one of two conditions is met: 1) the object's velocity drops below the threshold; or 2) the current walk does not meet a straightness requirement (operation 506). Upon one of these two conditions being met, the length and duration of the walk are assessed to determine if the walk should be analyzed for stride parameters and saved (operation 510). If the walk is saved, the state of the object returns to "not in walk" (operation 512). However, if the walk is not saved and the straightness requirement was the reason for termination, then the oldest points in the walk are iteratively discarded until the remaining points meet the straightness requirement. The state of the object is then returned to the in walk state (operation 514).

The straightness requirement consists of two measures: a global measure focused on the straightness of the entire path, and a local measure focused on abrupt changes. The first measure represents the average squared distance of each point in the sequence to a best fit line. The second measure represents the maximum deviation in walking direction computed over a small sliding window vs. that of the best fit line for the entire walk. Thresholds for both measures control the degree of straightness required for a walking sequence to be saved. In order to diminish the potential impact of capturing the beginning or the end of a walk on the computed average speed, only the middle 50 percent (based on time) of each walk is used to compute average speed.

The resulting output can be a dataset in which each entry corresponds to a walk identified in a given area. Each entry can be associated with the following features: height of the person, walking speeds, and, if possible, average stride time and average stride length, in addition to the time the walk occurred. Thus, each walk, $x_i$, is initially associated with either two or four features:

$$x_i = \begin{cases} \{h, s\} & \text{if no stride data} \\ \{h, s, st, sl\} & \text{else} \end{cases}$$

where h, s, st, and sl, are height, walking speed, stride time, and stride length, respectively. In order to include the information from walks without stride parameters in the computations, which due to furniture placement, etc., can make up the majority of walks in some areas (e.g. area 204), stride time and stride length values are estimated for the walks lacking them using the mean of the three nearest neighbors with stride information.

In one particular embodiment, the dataset can include walks from all the persons (e.g. person 202) of the area 204 (e.g. an apartment), as well as any visitors. As such, before any gait measurement estimates can be performed, a procedure for identifying walks from the specific person(s) is necessary.

One approach makes the assumption that each person will create a cluster, or mode, in the dataset, representing their typical, in-home, habitual gait. These clusters are modeled as Gaussian distributions in the 4D feature space. The basic procedure is to fit a Gaussian Mixture Model (GMM), $\lambda = \{\rho_r, \mu_r, \Sigma_r\}$, $r=1, \ldots, K$, with the number of distributions, K, equal to the number of persons 202 in the area 204 to the dataset, $X=\{x_1, \ldots, x_N\}$:

$$p(x_i|\lambda) = \sum_{r=1}^{k} \rho_r g(x_i|u_r, \Sigma_r)$$

where $g(x|\mu_r, \Sigma_r)$, $r=1, \ldots, K$, are the multivariate Gaussian distributions, and $\rho_r$, $r=1, \ldots, K$, are the mixture weights.

The Gaussian distribution representing of each person (e.g. person 202 such as a person) is used to identify walks from that particular person. Any walk whose likelihood given a distribution is greater than a threshold is assumed to be from the person that the distribution represents, and is used in computing gait parameter estimates for that person. The classification can be performed independently for each distribution. Thus, a walk could be included in the estimates of more than one person, if the distributions overlap. The steps of model initialization and updating are described below and illustrated in FIG. 2.

An output module 320 processes the depth image data 112 and/or the one or more generated parameters 114 to perform one or more health risk assessments. For example, the parameters 114 and depth image data 112 can be used to assess a patient's risk of falling and/or the onset of illness.

In one embodiment, the actual assessment of fall/health risk can be based on mapping the various gait parameters to standard clinical measures such as a Timed-up-and-Go (TUG) test, and the Habitual Gait Speed (HGS) test. For example, in one embodiment, a simple neural network model that can "predict" TUG time based on an individual person's average gait speed. It is contemplated that any gait parameter can be mapped to standard measures. For example, a TUG time above 16 or 20 seconds indicates a high risk of falling in the next year. Accordingly, the gait parameter data and/or gait parameter estimates can be used to predict a score that a person, such as a patient, would receive on various clinical measures, tests, and the like, such as the TUG, HGS, Berg Balance-Short Form, Short Physical Performance Battery, and Multi-Directional Reach Test data, etc.

Figure 4:
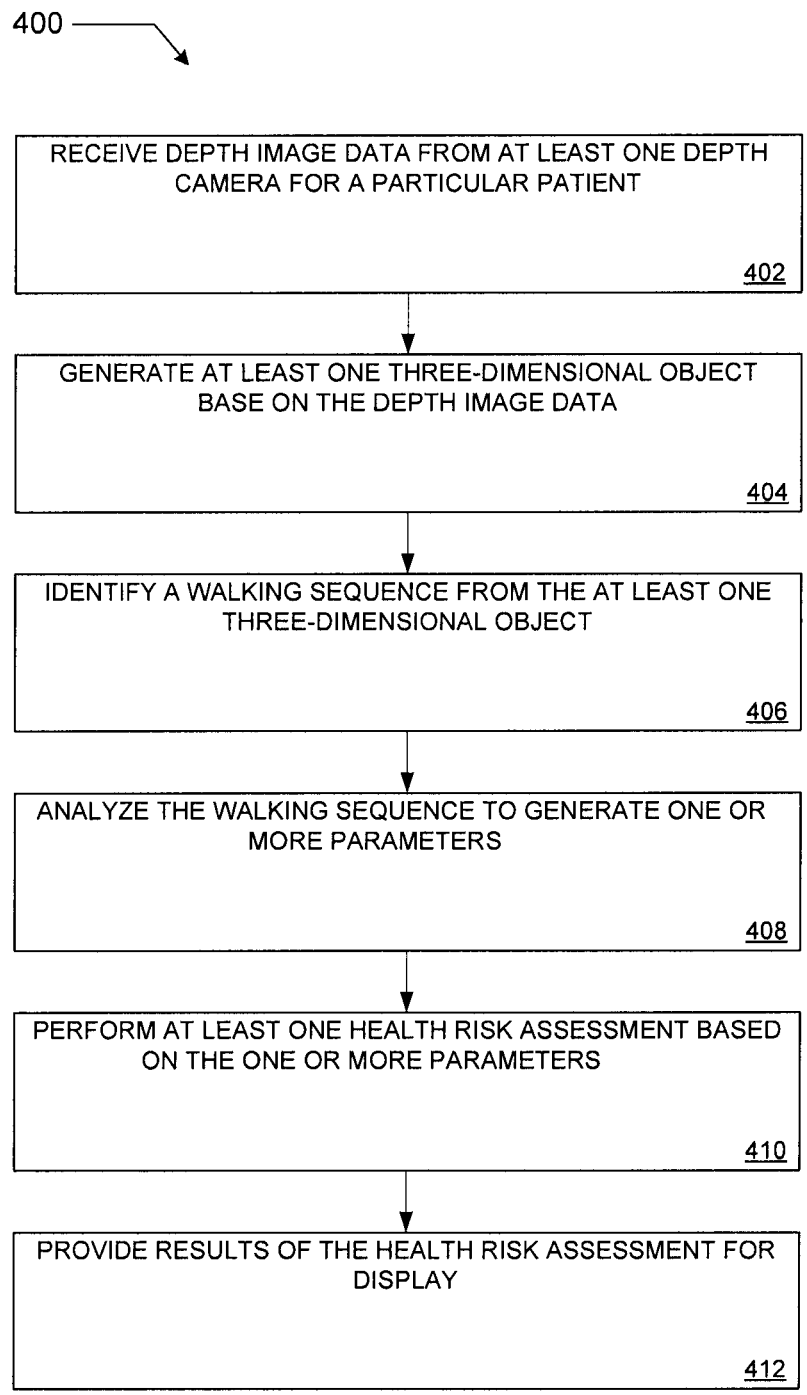
FIG. 4 is a flowchart illustrating an example for obtaining temporal and spatial gait parameters for performing health risk assessments, according to various embodiments of the present disclosure.

FIG. 4 depicts an example method and/or process 400 for obtaining depth image data and subsequently processing the depth image data to generate temporal and spatial gait parameters for use in health risk assessment. Process 400 can be executed by at least one processor encoded with, or executing instructions of, an image analysis application 109. Initially, at 402, process 400 includes receiving depth image data for a particular patient from one or more depth cameras 108. For example, depth image data can be received from a Microsoft Kinect™ camera device located in the home of an elderly gentleman. At 404, the depth image data can be analyzed to generate at least one three-dimensional object. For example, a three-dimensional representation of the elderly gentlemen patient can be generated. At 406, a walking sequence can be identified based on the at least one three-dimensional object. For example, a walking sequence corresponding to the elderly gentleman patient can be identified. At 408, one or more parameters can be generated from the walking sequence. For example, one or more temporal and spatial gait parameters can be generated corresponding to the elderly gentleman. At 410, the generated parameters are used to perform various health risk assessments for a particular patient (e.g. the elderly gentlemen) and results of the health risk assessments can be provided for display at 412.

Figure 4A:
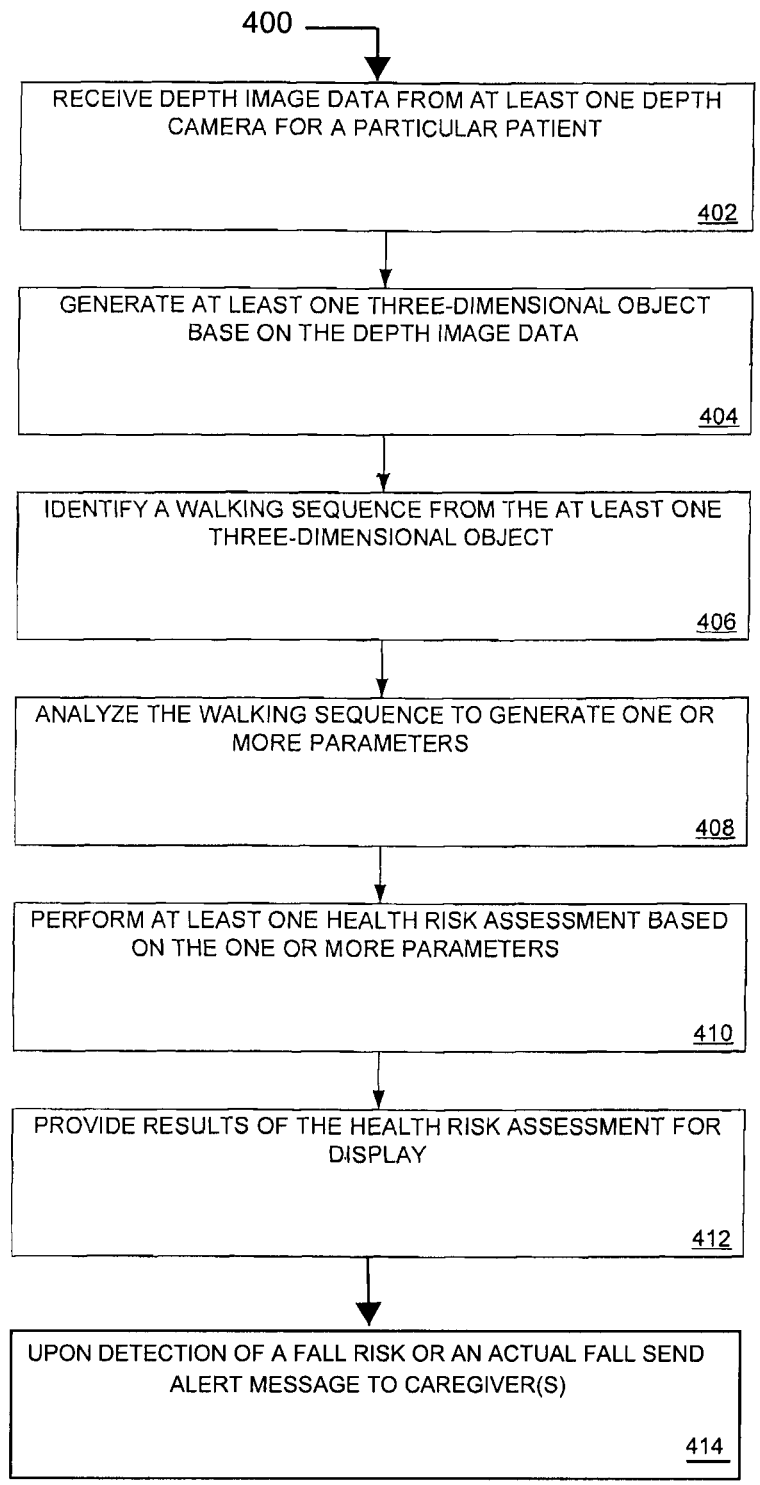
FIG. 4A is a flowchart illustrating an example for obtaining temporal and spatial gait parameters, performing health risk assessments, and sending a an alert if a fall is detected, according to various embodiments of the present disclosure.

Referring now to FIG. 4A, in various embodiments, the image analysis application 109 can additionally include an alert module 321 (shown in FIG. 3). In such embodiments, if operation of the system 100 and execution of the image analysis application 109, as described above, generates a health risk assessment indicating that a high risk of falling is present or detects that an actual fall has occurred, in addition to providing the health risk assessment results for display, as indicated at 412, execution of the alert module 321 will send and alert message to a programmable list of caregivers, e.g., doctors and/or family members, as indicated at 414. The alert message can be in any form and/or format suitable for alerting the list of caregivers. For example, the alert can be a visual message (e.g., a flashing light and/or an email and/or a text message), and/or an audible message (e.g., a beep or selected ringtone) and/or a tactile message (e.g., vibration of smartphone) sent to the caregivers(s) via a smartphone, desktop or laptop computer, computer tablet, television or any other suitable personal data/communication device connected to the central processing device 106 via the Internet 104 or any of the network systems described above.

Additionally, in various embodiments, the alert message can contain information about the fall or the detection of a high risk of falling, such as confidence of detection, time of occurrence of the incident (i.e., the recorded depth image data) that evoked the alert message, location of the incident that evoked the alert message, presence of another person besides the patient in the room at the time of the incident that evoked the alert message. Furthermore, in various embodiments, the alert message can include a hyperlink to video data, stored on the database 110, containing the depth imagery of the detected incident. In such embodiments, the video data can be any suitable type of video data, such as digital video data, analog video data, voxel (volume element) image video data, or some combination thereof. Still further, such video data can be playable and viewed using any suitable media player software, e.g., a media player program or computer app, whereby the video can be rewound, replayed and fast forwarded to allow the caregiver(s) to review the depth imagery in detail over a specified time period. Such a video hyperlink feature with the rewind, replay and fast forward capability can aid the caregiver(s), e.g., doctors, in determining whether emergency assistance is required and/or whether additional diagnostic tests are warranted, e.g., testing for stroke, testing for heart attack, X-rays, etc.

As used herein voxel data represents data values on a regular grid in three dimensional space. Voxel is a combination of "volumetric" and "pixel" where pixel is a combination of "picture" and "element". As with pixels in a bitmap, voxels themselves do not typically have their position (i.e., their coordinates) explicitly encoded along with their values. Instead, the position of a voxel is inferred based upon its position relative to other voxels (i.e., its position in the data structure that makes up a single volumetric image). Voxels are effectively utilized to represent regularly sampled spaces that are non-homogeneously filled.

The description above includes example systems, methods, techniques, instruction sequences, and/or computer program products that embody techniques of the present disclosure. However, it is understood that the described disclosure can be practiced without these specific details. In the present disclosure, the methods disclosed can be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure can be provided as a computer program product, or software, that can include a machine-readable medium having stored thereon instructions which can be used to program a computer system (or other electronic devices) to perform a process according to the present disclosure. A machine-readable medium includes any mechanism for storing information in a form (e.g., software, processing application) readable by a machine (e.g., a computer). The machine-readable medium can include, but is not limited to, magnetic storage medium (e.g., floppy diskette); optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions.

It is believed that the present disclosure and many of its attendant advantages will be understood by the foregoing description, and it will be apparent that various changes can be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various exemplary embodiments, it will be understood that these embodiments are illustrative and that the scope of the disclosure is not limited to them. Many variations, modifications, additions, and improvements are possible. More generally, embodiments in accordance with the present disclosure have been described in the context of exemplary implementations. Functionality can be separated or combined in blocks differently in various embodiments of the disclosure or described with different terminology. These and other variations, modifications, additions, and improvements can fall within the scope of the disclosure as defined in the claims that follow.

What is claimed is:

1. A method for determining the risk of a person to falling, the method comprising:
acquiring by at least one processor of a computer-based remote device, depth image data from at least one depth camera, wherein the depth image data comprises a plurality of frames that depict the person moving within an observation environment over time, the frames comprising a plurality of pixels, the remote device located remotely from the at least one depth camera, the remote device comprising electronic memory on which an image analysis application is electronically stored, and the at least one processor structured and operable to execute the image analysis application;
extracting, by the at least one processor, a foreground object from the depth image data;
segmenting, by the at least one processor, the pixels of the frames of the depth image data corresponding to the foreground object;
generating, by the at least one processor, a three-dimensional data object based on the foreground object, the three-dimensional data object representative of the person within the observation environment;
tracking, by the at least one processor, the three-dimensional data object over a plurality of frames of the depth images data; and
determining, by the at least one processor, that the person is walking within the observation environment, wherein the determining the person is walking comprises:
determining, by the at least one processor, a speed for the tracked three-dimensional data object over a time frame;
comparing, by the at least one processor, the determined speed with a speed threshold; and
stipulating the person to be walking wherein the determined speed is greater than the speed threshold;
assigning, by the at least one processor, a state indicative of the walking to the tracked three-dimensional data object;
then, once the person has been determined to be walking and the tracked three-dimensional object has been assigned a state indicative of walking:
determining, by the at least one processor, a walk straightness for the tracked three-dimensional data object;
determining, by the at least one processor, a walk length for the tracked three-dimensional data object;
determining, by the at least one processor, a walk duration for the tracked three-dimensional data object;
identifying and saving, by the at least one processor, the tracked three-dimensional data object in memory as a walking sequence when the determined walk straightness exceeds a straightness threshold, the determined walk length exceeds a walk length threshold, and the determined walk duration exceeds a walk duration threshold;

generating, by the at least one processor, one or more gait parameters from the identified walking sequence; and determining a level of risk at which the person is of falling by comparing, by the at least one processor, the one or more gait parameters against a standard clinical measure of the one or more gait parameters.

2. The method of claim 1, wherein the identified walking sequence is compared against a previously saved walking sequence of the person to confirm that the identified walking sequence is correctly associated with the person.

3. The method of claim 2, wherein the comparison utilizes a Gaussian distribution.

4. The method of claim 1, wherein the one or more gait parameters includes at least one of: walking speed, stride time, or stride length.

5. The method of claim 1, wherein the standard clinical measure is selected from the group consisting of: Timed-Up-and-Go (TUG) and Habitual Gait Speed (HGS).

* * * * *

UNITED STATES PATENT AND TRADEMARK OFFICE
CERTIFICATE OF CORRECTION

PATENT NO. : 10,080,513 B2
APPLICATION NO. : 15/424375
DATED : September 25, 2018
INVENTOR(S) : Erik Edward Stone et al.

It is certified that error appears in the above-identified patent and that said Letters Patent is hereby corrected as shown below:

In the Specification

Under Column 1, beginning with Line 24, before the heading FIELD, insert the following heading and statement:
--GOVERNMENT RIGHTS
This invention was made with government support under CNS-0931607 awarded by the National Science Foundation, and under 5R01HS018477 awarded by the Agency for Healthcare Research and Quality. The government has certain rights in the invention.--

Signed and Sealed this
Fourteenth Day of May, 2019

Andrei Iancu
*Director of the United States Patent and Trademark Office*